US008785484B2

(12) United States Patent
Brossard et al.

(10) Patent No.: US 8,785,484 B2
(45) Date of Patent: Jul. 22, 2014

(54) DOSING REGIMEN FOR A SELECTIVE S1P1 RECEPTOR AGONIST

(75) Inventors: Patrick Brossard, Allschwil (CH);
Jasper Dingemanse, Allchwil (FR);
Oliver Nayler, Arlesheim (CH);
Michael Scherz, Ettingen (CH); Beat Steiner, Dornach (CH)

(73) Assignee: Actelion Pharmaceuticals Ltd, Allschwill (CH)

( * ) Notice: Subject to any disclaimer, the term of this patent is extended or adjusted under 35 U.S.C. 154(b) by 518 days.

(21) Appl. No.: 12/922,777

(22) PCT Filed: Mar. 12, 2009

(86) PCT No.: PCT/IB2009/051030
§ 371 (c)(1),
(2), (4) Date: Sep. 15, 2010

(87) PCT Pub. No.: WO2009/115954
PCT Pub. Date: Sep. 24, 2009

(65) Prior Publication Data
US 2011/0021581 A1 Jan. 27, 2011

(30) Foreign Application Priority Data

Mar. 17, 2008 (WO) .................. PCT/IB2008/050995

(51) Int. Cl.
A61K 31/425 (2006.01)
A61K 31/00 (2006.01)
A61K 31/426 (2006.01)

(52) U.S. Cl.
CPC ............... A61K 31/00 (2013.01); A61K 31/426 (2013.01)
USPC ........................................................ 514/369

(58) Field of Classification Search
USPC ........................................................ 514/369
See application file for complete search history.

(56) References Cited

U.S. PATENT DOCUMENTS

| 7,435,828 | B2 * | 10/2008 | Binkert et al. ................. 548/184 |
| 7,626,037 | B2 | 12/2009 | Binkert et al. |
| 7,875,726 | B2 | 1/2011 | Binkert et al. |
| 7,879,821 | B2 * | 2/2011 | Hauser ............................. 514/58 |
| 8,263,780 | B2 | 9/2012 | Abele et al. |
| 8,273,779 | B2 | 9/2012 | Binkert et al. |
| RE43,728 | E | 10/2012 | Binkert et al. |
| RE43,833 | E | 11/2012 | Binkert et al. |
| 8,524,752 | B2 | 9/2013 | Binkert et al. |
| 2007/0082933 | A1 | 4/2007 | Binkert et al. |
| 2008/0146629 | A1 | 6/2008 | Binkert et al. |
| 2008/0280962 | A1 | 11/2008 | Binkert et al. |
| 2009/0275625 | A1 | 11/2009 | Binkert et al. |
| 2010/0160259 | A1 | 6/2010 | Schmouder |
| 2011/0039818 | A1 | 2/2011 | Legangneux |
| 2011/0196004 | A1 | 8/2011 | Bonham et al. |
| 2011/0257133 | A1 | 10/2011 | Schmouder |
| 2012/0302758 | A1 | 11/2012 | Abele et al. |

FOREIGN PATENT DOCUMENTS

| JP | T-2005-535679 | 11/2005 |
| WO | WO 2004/010987 | 2/2004 |
| WO | WO 2005/054215 | 6/2005 |
| WO | WO 2005/123677 | 12/2005 |
| WO | WO 2006/010544 | 2/2006 |
| WO | WO 2006/058316 | 6/2006 |
| WO | WO 2006/100631 | 9/2006 |
| WO | WO 2006/100633 | 9/2006 |
| WO | WO 2006/100635 | 9/2006 |
| WO | WO 2006/137019 | 12/2006 |
| WO | WO 2007/060626 | 5/2007 |
| WO | WO 2007/080542 | 7/2007 |
| WO | WO 2007/086001 | 8/2007 |
| WO | WO 2008/029306 | 3/2008 |
| WO | WO 2008/029370 | 3/2008 |
| WO | WO 2008/029371 | 3/2008 |
| WO | WO 2008/035239 | 3/2008 |
| WO | WO 2008/114157 | 9/2008 |
| WO | WO 2009/024905 | 2/2009 |
| WO | WO 2010/072703 | 7/2010 |
| WO | WO 2010/075239 | 7/2010 |

OTHER PUBLICATIONS

U.S. Appl. No. 12/516,055, filed May 22, 2009, Abele, et al.
"Actelion's Orally Active Selective S1P1 Receptor Agonist to be Jointly Developed/Promoted with Roche in Autoimmune Disorders and Transplantation; Deal Potentially Worth Well Over US$630 Million to Actelion", http://www.mskreport.com/print.cfm?articleID=827. Jul. 20, 2006.
Bunemann, M., et al., "Activation of Muscarinic K+Current in Guinea-pig Atrial Myocytes by Sphingosine-1-phosphate", Journal of Physiology, vol. 489, pp. 701-707, (1995).
Davidov, T., et al., "Chronic Nitric Oxide Synthase Blockade Desensitizes the Heart to the Negative Metabolic Effects of Nitric Oxide", Life Sciences, Pergamon Press, Oxford, GB, vol. 79, pp. 1674-1680, (2006).
Frolkis, V.V., "The Role of 'Invertors' (Intracellular Activators) in Age-related Changes in Cell Response to Hormones", Experimental Gerontology, vol. 30, pp. 401-414, (1995).

(Continued)

Primary Examiner — Jennifer M Kim
(74) Attorney, Agent, or Firm — Hoxie & Associates LLC

(57) ABSTRACT

The present invention relates to a dosing regimen for a selective S1P$_1$ receptor agonist, whereby the selective S1P$_1$ receptor agonist is administered to a subject in such a way that during the initial treatment phase the selective S1P$_1$ receptor agonist is administered at a dose which induces desensitization of the heart wherein said dose is below the target dose, and at a dosing frequency that sustains desensitization of the heart, until no further acute heart rate reduction occurs, followed by dose up-titration to the target dose of the selective S1P$_1$ receptor agonist.

10 Claims, No Drawings

(56) References Cited

OTHER PUBLICATIONS

Fujishiro, J., et al., "Use of Sphingosine-1-Phosphate 1 Receptor Agonist, KRP-203, in Combination with a Subtherapeutic Dose of Cyclosporine A for Rat Renal Transplantation", Transplantation, vol. 82(6), pp. 804-812, (2006).

Gould, P.L., "Salt Selection for Basic Drugs", International Journal of Pharmaceutics, vol. 33, pp. 201-217, (1986).

Guo, J., et al., "Effects of Sphingosine 1-phosphate on Pacemaker Activity in Rabbit Sino-atrial Node Cells", Pflugers Arch, vol. 438, pp. 642-648, (1999).

Hale, J., et al., "Selecting Against $S1P_3$ Enhances the Acute Cardiovascular Tolerability of 3-(N-benzyl)aminopropylphosphonic Acid S1P Receptor Agonists", Bioorganic & Medicinal Chemistry Letters, vol. 14(13), pp. 3501-3505, (2004).

Himmel, H., et al., "Evidence for Edg-3 Receptor-Mediated Activation of $I_{K,Ach}$ by Sphingosine-1-Phosphate in Human Atrial Cardiomyocytes", Molecular Pharmacology, vol. 58, pp. 449-454, (2000).

Huwiler, A., et al., "New Players on the Center Stage: Sphingosine 1-Phosphate and its Receptors as Drug Targets", Biochemical Pharmacology, Pergamon Press, Oxford, GB, vol. 75, pp. 1893-1900, (2008).

Kappos, L., et al., "Oral Fingolimod (FTY720) for Relapsing Multiple Sclerosis", The New England Journal of Medicine, vol. 355(11), pp. 1124-1140, (2006).

Kovarik, J.M., et al., "A Mechanistic Study to Assess Whether Isoproterenol Can Reverse the Negative Chronotropic Effect of Fingolimod", Journal of Clinical Pharmacology, vol. 48, No. 3, pp. 303-310, (2008).

Koyrakh, L., et al., "The Heart Rate Decrease Caused by Acute FTY720 Administration is Mediated by the G Protein-Gated Potassium Channel $1_{KACh}$", American Journal of Transplantation, vol. 5, pp. 529-536, (2005).

Ochi, R., et al., "Sphingosine-1-Phosphate Effects on Guinea Pig Atrial Myocytes: Alterations in Action Potentials and $K^+$Currents", Cardiovascular Research, vol. 70, pp. 88-96, (2006).

Peters, S., et al., "Sphingosine-1-Phosphate Signaling in the Cardiovascular System", Current Opinion in Pharmacology, vol. 7(2), pp. 186-192, (2007).

Remington, The Science and Practice of Pharmacy, $21^{st}$ Edition (2005), Part 5, "Pharmaceutical Manufacturing" [published by Lippincott Williams & Wilkins].

Sanna, M.G., et al., "Sphingosine 1-Phosphate (S1P) Receptor Subtypes $S1P_1$ and $S1P_3$, Respectively, Regulate Lymphocyte Recirculation and Heart Rate", The Journal of Biological Chemistry, vol. 279(14), pp. 13839-13848, (2004).

Huwiler, A., et al., "New Players on the Center Stage: Sphingosine 1-phosphate and its receptors as drug targets", Biochemical Pharmacology, Pergamon, Oxford, GB, vol. 75, No. 10, Jan. 5, 2008, pp. 1893-1900.

Anonymous, "Actelion's Orally Active Selective S1P1 Receptor Agonist to be Jointly Developed/Promoted with Roche in Autoimmune Disorders and Transplantation Deal Potentially Worth Well Over US$630 Million to Actelion", Musculoskeletal Report, [Online], Jul. 20, 2006, pp. 1, New York, NY 10016, USA, Retrieved from the Internet: URL: http://www.mscreport.com/print.cfm?articleID=827>.

Kovarik, J., M., et al., "A Mechanistic Study to Access Whether Isoproterenol Can Reverse the Negative Chronotropic Effect of Fingolimod", Journal of Clinical Pharmacology, vol. 48, No. 3, Jan. 24, 2008, pp. 303-310.

Davidov, T., et al., "Chronic Nitric Oxide Synthase Blockade Desensitizes the Heart to the Negative Metabolic Effects of Nitric Oxide", Life Sciences, Pergamon Press, Oxford, GB, vol. 79, No. 17, Sep. 20, 2006, pp. 1674-1680.

Frolkis, V.V., "The Role of "Invertors" (Intracellular Activators In Age-Related Changes in Cell Response to Hormones", Experimental Gerontology, vol. 30, No. 3-4, 1995, pp. 401-414.

Schmouder et al. "FTY720: Placebo-Controlled Study of the Effect on Cardiac Rate and Rhythm in Healthy Subjects" Journal of Clinical Pharmacology, vol. 46, pp. 895-904 (2006).

Keller et al. "Immunomodulator FTY720 Induces Myofibroblast Differentiation via the Lysophospholipid Receptor S1P3 and Smad3 Signaling" The American Journal of Pathology, vol. 170, No. 1, pp. 281-292 (2007).

Brinkmann, V. "Sphingosine 1-Phosphate Receptors in Health and Disease: Mechanistic Insights from Gene Deletion Studies and Reverse Pharmacology", Pharmacol. Ther. (2007), vol. 115, pp. 84-105, (doi:10.1016/j.pharmathera.2007.04.006).

U.S. Appl. No. 13/951,954, filed Jul. 26, 2013, Christoph Binkert, et al.

U.S. Appl. No. 14/028,712, filed Sep. 17, 2013, Christoph Binkert, et al.

\* cited by examiner

DOSING REGIMEN FOR A SELECTIVE S1P1 RECEPTOR AGONIST

CROSS REFERENCE TO RELATED APPLICATIONS

This application is a United States Application under 35 U.S.C. 371 claiming benefit of PCT Application No. PCT/IB2009/051030, filed on Mar. 12, 2009, which claims the benefit of PCT Application No. PCT/IB2008/050995, filed on Mar. 17, 2008, the contents of each of which are incorporated herein by reference.

FIELD OF THE INVENTION

The present invention relates to a dosing regimen for a selective $S1P_1$ receptor agonist, whereby the selective $S1P_1$ receptor agonist is administered to a subject in such a way that during the initial treatment phase the selective $S1P_1$ receptor agonist is administered at a dose which induces desensitization of the heart wherein said dose is below the target dose, and at a dosing frequency that sustains desensitization of the heart, until no further acute heart rate reduction occurs, followed by dose up-titration to the target dose of the selective $S1P_1$ receptor agonist. The present invention also provides a kit containing different units of medication of a selective $S1P_1$ receptor agonist for administration according to the invention, whereby one or more units of a dose strength below the target dose of said selective $S1P_1$ receptor agonist are provided for the initial treatment phase, and subsequent units of medication of higher dose strengths up to the target dose of said selective $S1P_1$ receptor agonist are provided.

BACKGROUND OF THE INVENTION

The present invention provides a dosing regimen for a selective $S1P_1$ receptor agonist, by which adverse effects are minimized in subjects/patients during the initial treatment phase, or upon re-initiation of dosing after drug discontinuation.

Selective $S1P_1$ receptor agonists are compounds which preferentially activate the human $S1P_1$ receptor sub-type from among the $S1P_1$, $S1P_2$, $S1P_3$, $S1P_4$, and $S1P_5$ family members of sphingosine-1-phosphate-sensitive human G-protein coupled receptors. S1P receptor agonists decrease the number of circulating lymphocytes in peripheral blood in humans or animals after e.g. oral administration, therefore they have therapeutic potential in a variety of diseases associated with a dysregulated immune system. For example, the non-selective S1P receptor agonist FTY720 has been found to reduce the rate of clinical relapses in multiple sclerosis patients (Kappos L et al., *N Engl J Med.* 2006 Sep. 14, 355(11): 1124-40).

However, S1P receptor agonists have been described to reduce heart rate in rodent animal models, an effect that has been attributed to the activation of the $S1P_3$ receptor in the sinoatrial nodal tissue of the heart, which increases the $I_{K,ACh}$ inward rectifier current, and slows the sinoatrial pacemaker (Hale J J et al., *Bioorg Med Chem Lett.* 2004, 14(13): 3501-5; Bünemann M et al., *J Physiol* 1995, 489: 701-707; Guo J et al., *Pflugers Arch* 1999, 438: 642-648; Ochi R et al., *Cardiovasc Res* 2006, 70: 88-96). Moreover, the non-selective S1P receptor agonist FTY720 reduces heart rate in humans (Koyrakh L et al., *Am J Transplant* 2005, 5: 529-536), and the literature suggests that $S1P_1$ selective compounds would have diminished effects on heart rate in humans, compared to non-selective S1P receptor agonists (Himmel H M et al., *Mol Pharmacol* 2000, 58: 449-454; Peters S L, Alewijnse A E, *Curr Opin Pharmacol.* 2007, 7(2): 186-92; Fujishiro J et al., *Transplantation* 2006, 82(6): 804-12; Sanna M G et al., *J Biol Chem.* 2004, 279(14): 13839-48).

DESCRIPTION OF THE INVENTION

The compound (R)-5-[3-chloro-4-(2,3-dihydroxy-propoxy)-benz[Z]ylidene]-2-([Z]-propylimino)-3-o-tolyl-thiazolidin-4-one (hereinafter also referred to as "Compound 1"; the preparation of Compound 1 and the medicinal use thereof, is described in the published PCT application WO 2005/054215) is a selective $S1P_1$ receptor agonist, and repeated daily oral dosing of 5 mg or more to humans results in a consistent, sustained, and dose-dependent reduction in the number of peripheral blood lymphocytes. It has been surprisingly found, however, that the selective $S1P_1$ receptor agonist Compound 1 transiently reduces heart rate in humans, with maximal effects 1-3 hours after administration. In some individuals this is accompanied by similarly transient increases in the PR interval in the electrocardiogram (ECG), and an associated irregular heart rhythm (so-called Wenckebach rhythm). Occasional fatigue or dizziness also occur in the post-dose period. These acute effects of Compound 1 on heart rate and rhythm and fatigue/dizziness are milder at 10 mg than at 20 mg. All of these effects wane with repeated dosing. Thus, after 2 to 4 days of daily oral doses of 5 to 20 mg, an acute heart rate reduction, compared to the pre-dose value, is no longer observed upon administration of Compound 1. Similarly, with repeated daily oral dosing of 5 to 20 mg of Compound 1, transient increases in the PR interval of the ECG relative to pre-dose values are not observed, nor are fatigue or dizziness reported. The acute effects on heart rate, atrioventricular conduction, or fatigue and dizziness, although not seriously adverse, are undesirable, and methods to minimize these effects would be valuable for maximizing the tolerability and safety of Compound 1, and other selective $S1P_1$ receptor agonists, and minimizing associated monitoring requirements, in the early phase of dosing initiation, or, after a drug interruption, at re-initiation of drug therapy.

The subject matter of the present invention therefore provides a dosing regimen for selective $S1P_1$ receptor agonists, such as and especially Compound 1, which minimizes the incidence or severity of the stated adverse effects. The dosing regimen of the present invention provides that a selective $S1P_1$ receptor agonist is administered to a subject in such a way that during the initial treatment phase the selective $S1P_1$ receptor agonist is administered at a dose which induces desensitization of the heart wherein said dose is below the target dose, and at a dosing frequency that sustains desensitization of the heart, until no further acute heart rate reduction occurs, followed by dose up-titration to the target dose of the selective $S1P_1$ receptor agonist. The dosing regimen of the present invention has the advantage that a desensitization of the heart can be induced and sustained at a dose below the target dose with less pronounced acute heart rate reduction when compared to giving the target dose without such a dosing regimen. The dosing regimen of the present invention therefore results in an improved tolerability by minimizing the adverse effects in subjects/patients during the first days of dosing of a selective $S1P_1$ receptor agonist, or upon re-initiation of dosing after drug discontinuation.

The choice of the dosing regimen (i.e., the magnitude of the dose and the dosing frequency) during the initial treatment period can be arrived at empirically, by comparing the magnitude of the acute heart rate reduction between initial doses given. The dosing frequency should be convenient for the patient, it should be longer than the duration of the acute heart rate reduction, and it should be shorter than the time required for the heart to recover from desensitization. The thus empirically chosen dosing frequency, will reflect the relative rate constants of several independent processes: the rate constant for the concentration of the $S1P_1$ receptor agonist in the body to exceed a concentration threshold associated with desensitization; the rate constant for desensitization of the heart; and the rate constant for the recovery from desensitization of the heart. The latter two rate constants (for desensitization of the heart, and for recovery from desensitization) are intrinsic properties of the underlying biological processes that give rise to these phenomena. The first rate constant (for exceeding the concentration threshold) is determined by the pharmacokinetics of the $S1P_1$ receptor agonist, i.e., on the rates of absorption, distribution, metabolism and excretion of the drug. In view of the above-mentioned three rate constants, the duration of a suitable dosing interval will be dose-dependent.

For example, Compound 1, when given as a 20-mg once-daily dose by the oral route, results in an acute heart rate reduction on Day 1, and when the second 20-mg dose is administered 24 hours later, no acute heart rate reduction is observed. Desensitization has been sustained over this 24-hour dosing interval. Yet, when a second 20-mg dose is administered 7 days after the first dose, it results in an acute heart rate reduction of similar magnitude as on Day 1. Desensitization has not been sustained over this 7-day dosing interval of the 20-mg dose. This example illustrates that a suitable dosing interval is necessary to sustain desensitization of the heart.

i) In particular, the present invention relates to a selective $S1P_1$ receptor agonist for use as a medicament, whereby said selective $S1P_1$ receptor agonist is administered to a subject (especially a human subject) in such a way that during the initial treatment phase the selective $S1P_1$ receptor agonist is administered at a dose which induces desensitization of the heart wherein said dose is below the target dose, and at a dosing frequency that sustains desensitization of the heart, until no further acute heart rate reduction occurs, followed by dose up-titration to the target dose of the selective $S1P_1$ receptor agonist.

ii) In a further embodiment, the present invention relates to the selective $S1P_1$ receptor agonist for use as a medicament according to embodiment i), whereby the initial dose below the target dose is between 2- to 5-fold lower than the target dose.

iii) In a further embodiment, the present invention relates to the selective $S1P_1$ receptor agonist for use as a medicament according to embodiment i), whereby the initial dose below the target dose is between 5- to 16-fold lower than the target dose.

iv) In a further embodiment, the present invention relates to the selective $S1P_1$ receptor agonist for use as a medicament according to any one of embodiments i) to iii), whereby a dose below the target dose is administered to the subject during the initial 2 to 4 days of the treatment.

v) In a further embodiment, the present invention relates to the selective $S1P_1$ receptor agonist for use as a medicament according to any one of embodiments i) to iv), whereby the dose below the target dose is administered at a dosing frequency of once or twice daily.

vi) In a further embodiment, the present invention relates to the selective $S1P_1$ receptor agonist for use as a medicament according to any one of embodiments i) to v), wherein the selective $S1P_1$ receptor agonist is (R)-5-[3-chloro-4-(2,3-dihydroxy-propoxy)-benz[Z]ylidene]-2-([Z]-propylimino)-3-o-tolyl-thiazolidin-4-one, or a pharmaceutically acceptable salt thereof.

vii) In a further embodiment, the present invention relates to the use of a selective $S1P_1$ receptor agonist in the manufacture of a medicament, whereby said medicament is administered to a subject as specified in any one of embodiments i) to v).

viii) In a further embodiment, the present invention relates to the use according to embodiment vii), wherein the selective $S1P_1$ receptor agonist is (R)-5-[3-chloro-4-(2,3-dihydroxy-propoxy)-benz[Z]ylidene]-2-([Z]-propylimino)-3-o-tolyl-thiazolidin-4-one, or a pharmaceutically acceptable salt thereof.

ix) The present invention also relates to a kit containing different units of medication of a selective $S1P_1$ receptor agonist for administration according to embodiment i), whereby one or more units of a dose strength below the target dose of said selective $S1P_1$ receptor agonist are provided for the initial treatment phase, and subsequent units of medication of higher dose strengths up to the target dose of said selective $S1P_1$ receptor agonist are provided.

x) In a further embodiment, the present invention relates to the kit according to embodiment ix), wherein the selective $S1P_1$ receptor agonist is (R)-5-[3-chloro-4-(2,3-dihydroxy-propoxy)-benz[Z]ylidene]-2-([Z]-propylimino)-3-o-tolyl-thiazolidin-4-one, or a pharmaceutically acceptable salt thereof.

xi) In a further embodiment, the present invention relates to the kit according to embodiment ix) or x), whereby subsequent units of medication of 2- to 5-fold higher dose strengths compared to the initial dose strength are provided.

xii) In a further embodiment, the present invention relates to the kit according to embodiment ix) or x), whereby subsequent units of medication of 5- to 16-fold higher dose strengths compared to the initial dose strength are provided.

xiii) In a further embodiment, the present invention relates to the kit according to any one of embodiments ix) to xii), whereby the dose strength units below the target dose are provided for the initial 2 to 4 days of treatment.

xiv) In a further embodiment, the present invention relates to the kit according to any one of embodiments ix) to xiii), whereby the dose strength unit(s) below the target dose is/are administered at a dosing frequency of once or twice daily.

xv) The present invention further also relates to a method for administering a selective $S1P_1$ receptor agonist, whereby the selective $S1P_1$ receptor agonist is administered to a subject as specified in any one of embodiments i) to v).

xvi) In a further embodiment, the present invention relates to the method according to embodiment xv), wherein the selective $S1P_1$ receptor agonist is (R)-5-[3-chloro-4-(2,3-dihydroxy-propoxy)-benz[Z]ylidene]-2-([Z]-propylimino)-3-o-tolyl-thiazolidin-4-one, or a pharmaceutically acceptable salt thereof.

The general terms used hereinbefore and hereinafter preferably have, within this disclosure, the following meanings:

The term "desensitization of the heart" as used herein refers to the absence of an acute heart rate reduction after drug administration.

The term "acute heart rate reduction" as used herein refers to a heart rate decrease from pre-dose values of, for example, 10 or more beats per minute (bpm), that is maximal within a few hours, for example 1-3 hours, after drug administration, and thereafter the heart rate returns towards the pre-dose value.

The term "target dose" as used herein refers to the dose of a selective $S1P_1$ receptor agonist that achieves target peripheral blood lymphocyte counts, e.g., 400-800 lymphocytes per microliter. The target dose for a given $S1P_1$ receptor agonist may vary depending on the nature and severity of the disease to be treated.

Dose up-titration to the target dose can be achieved in one or several dose increments. For example, a suitable dosing regimen for Compound 1 can be 5 mg p.o. (once daily for 3 days; the initial treatment phase), followed by up-titration to 10 mg p.o. (once daily for 3 days), followed by up-titration to 20 mg p.o. (the target dose) given once daily indefinitely. Another example of a suitable dosing regimen for Compound 1 can be 5 mg p.o. (once daily for 3 days; the initial treatment phase), followed by up-titration to 20 mg p.o. (the target dose) given once daily indefinitely.

Selective $S1P_1$ receptor agonists according to the present invention are compounds which preferentially activate the human $S1P_1$ receptor sub-type from among the $S1P_1$, $S1P_2$, $S1P_3$, $S1P_4$, and $S1P_5$ family members, especially compounds which possess a potency for activation of the $S1P_1$ receptor over the other family members of at least 5-fold in a suitable assay. Such suitable assays to determine S1P receptor agonist activities are known in the art. In particular, $S1P_1$ receptor agonist activity of a compound can be tested using the GTPγS assay as described for example in WO 2007/080542 for the human $S1P_1$ receptor. The same assay can be used to determine the agonist activities of a compound regarding the other S1P family members by using CHO cells expressing recombinant human $S1P_2$, $S1P_3$, $S1P_4$, and $S1P_5$ receptors, respectively.

Preferred selective $S1P_1$ receptor agonists according to the present invention, their preparation and medicinal use are disclosed in the published PCT applications WO 2005/054215, WO 2005/123677, WO 2006/010544, WO 2006/100635, WO 2006/100633, WO 2006/100631, WO 2006/137019, WO 2007/060626, WO 2007/086001, WO 2007/080542, WO 2008/029371, WO 2008/029370, WO 2008/029306, WO 2008/035239, WO 2008/114157, and WO 2009/024905.

The selective $S1P_1$ receptor agonists and their pharmaceutically acceptable salts, can be used as a medicament, e.g., in the form of pharmaceutical compositions for enteral or parenteral administration, and are suitable for the prevention and/or treatment of diseases or disorders associated with an activated immune system.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the selective $S1P_1$ receptor agonists or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

Such diseases or disorders associated with an activated immune system which can be treated and/or prevented with selective $S1P_1$ receptor agonists are described for example in WO 2005/054215.

Preferred diseases or disorders to be treated and/or prevented with selective $S1P_1$ receptor agonists are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; type I diabetes; post-infectious autoimmune diseases including rheumatic fever and post-infectious glomerulonephritis; solid cancers; and tumor metastasis.

Particularly preferred diseases or disorders to be treated and/or prevented with selective $S1P_1$ receptor agonists are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with selective $S1P_1$ receptor agonists are selected from multiple sclerosis and psoriasis.

Furthermore, selective $S1P_1$ receptor agonists are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, nonsteroidal anti-inflammatory drugs, cytotoxic drugs, adhesion molecule inhibitors, cytokines, cytokine inhibitors, cytokine receptor antagonists, and recombinant cytokine receptors.

To date, Compound 1 has been administered to humans in three Phase 1 studies. In total, 85 subjects have been treated with Compound 1, at single doses of up to 75 mg, and at multiple doses of up to 40 mg for up to 15 days.

In the single-ascending dose (SAD) study (AC-058-101), Compound 1 was administered orally to 6 groups of 6 healthy male subjects (aged 21-47 years). Doses of 1, 3, 8, 20, 50 and 75 mg were given to sequential groups of 8 subjects (6 on active drug and 2 on placebo) in a randomized, double-blind, placebo-controlled design. The dose of 20 mg was given once in the fasted and once in the fed condition, to assess any food effects on the pharmacokinetics of Compound 1. ECGs were recorded, clinical laboratory parameters, vital signs, pulmonary function, neurological assessments (in the 75-mg dose group), plasma levels of Compound 1, and peripheral lymphocyte counts (total and subsets) were determined. All 48 randomized subjects were evaluable and no subjects withdrew or discontinued from the study. All subjects treated with Compound 1 (n=36) were included in the pharmacokinetic (PK) and pharmacodynamic (PD) analysis.

In Part A of the multiple-ascending dose (MAD) study (AC-058-102), Compound 1 was administered orally with doses of 5, 10, and 20 mg once-daily for 7 days to healthy male and female subjects (aged 22-58 years, 1:1 sex ratio) in a randomized, double-blind, placebo-controlled design. At each dose level, a group of 10 subjects were randomized to Compound 1 (8), or placebo (2). In Part A, all 30 randomized subjects completed the study and the 24 subjects who were treated with Compound 1 were included in the PK analysis.

In Part B of the MAD study, an up-titration scheme was implemented in order to reduce first-dose effects of Compound 1 on sinus node automaticity and atrioventricular- (AV-) conduction. Treatment with Compound 1 started for 4 days with 10 mg once daily, followed by 4 days with 20 mg once daily, and 7 days with 40 mg once daily. Seventeen subjects (nine females and eight males, aged 18-43 years) were randomized. Thirteen subjects received active treatment and four subjects received matching placebo. A total of 15 out of the 17 subjects completed the study as scheduled. Dosing was discontinued in two subjects on active treatment due to adverse events, in one case a moderate tooth infection and edema in the mouth, and in the other, a moderate granulocyte shift to the left in the peripheral blood smear, which was already present at baseline. The 11 subjects treated with 40-mg Compound 1 who completed the study were included in the PK analysis of Compound 1.

Table 1 shows the comparison of the mean heart rate (HR) reduction at 2.5 h post-dose vs pre-dose in the 40-mg dose group (AC-058-102, Part B) after each titration step (Day 1 for 10 mg, Day 5 for 20 mg, and Day 9 for 40 mg) vs HR reduction without up-titration on Day 1 (10 and 20 mg Part A of AC-058-102 and 50 mg of AC-058-101).

TABLE 1

Comparison of the mean HR reduction at 2.5 h post-dose with and without up-titration

| Without up-titration | | With up-titration | |
|---|---|---|---|
| Part A (10 and 20-mg) and 50-mg SAD | Mean HR reduction (2.5 h post-dose vs baseline) | Part B (40-mg dose group) | Mean HR reduction (2.5 h post-dose vs pre-dose) |
| 10 mg | 14 bpm | 10 mg | 14 bpm |
| 20 mg | 22 bpm | 20 mg | 9 bpm |
| 50 mg | 18 bpm | 40 mg | 4 bpm |

The mean HR reduction at 2.5 h post-dose vs pre-dose in the 40-mg dose group (AC-058-102, Part B) on days 2, 3, and 4 (10 mg) was 2 bpm, 1 bpm, and 1 bpm, respectively, and 4 bpm, 3 bpm, and 3 bpm on days 6, 7, and 8 (20 mg), respectively.

During Part B of the study, only one subject reported a transient AV-block first degree after administration of the first 10 mg dose of Compound 1 on Day 1, suggesting that up-titration reduces the effects of Compound 1 on both sinus node automaticity and AV-conduction. No second or third degree AV-blocks were observed during Part B of the study. No relevant effects on other ECG variables were recorded with multiple dosing in Part B.

The invention claimed is:

1. A method for administering (R)-5-[3-chloro-4-(2,3-dihydroxy-propoxy)-benz[Z]ylidene]-2-([Z]-propylimino)-3-o-tolyl-thiazolidin-4-one (Compound 1), or a pharmaceutically acceptable salt thereof to a subject in need thereof, wherein, during the an initial treatment phase Compound 1, or a pharmaceutically acceptable salt thereof is administered at a dose which induces desensitization of the heart to acute heart rate reduction, said dose being below the target dose, and at a dosing frequency that sustains desensitization of the heart, until no further acute heart rate reduction occurs, followed by dose up-titration to the target dose of Compound 1, or a pharmaceutically acceptable salt thereof.

2. The method for administering Compound 1, or a pharmaceutically acceptable salt thereof, according to claim 1, wherein the dose in the initial treatment phase is between 2- to 5-fold lower than the target dose.

3. The method for administering Compound 1, or a pharmaceutically acceptable salt thereof, according to claim 1, wherein the dose in the initial treatment phase is between 5- to 16-fold lower than the target dose.

4. The method for administering Compound 1, or a pharmaceutically acceptable salt thereof, according to claim 1, wherein the dose below the target dose is administered to the subject during the initial 2 to 4 days of the treatment.

5. The method for administering Compound 1, or a pharmaceutically acceptable salt thereof, according claim 1, wherein the dose below the target dose is administered at a dosing frequency of once or twice daily.

6. The method for administering Compound 1, or a pharmaceutically acceptable salt thereof, according to claim 3, wherein the dose below the target dose is administered at a dosing frequency of once or twice daily.

7. The method for administering Compound 1, or a pharmaceutically acceptable salt thereof, according claim 1, wherein the target dose is 20 mg of Compound 1 administered p.o. once daily.

8. The method for administering Compound 1, or a pharmaceutically acceptable salt thereof, according to claim 3, wherein the target dose is 20 mg of Compound 1 administered p.o. once daily.

9. The method for administering Compound 1, or a pharmaceutically acceptable salt thereof, according to claim 5, wherein the target dose is 20 mg of Compound 1 administered p.o. once daily.

10. The method for administering Compound 1, or a pharmaceutically acceptable salt thereof, according to claim 6, wherein the target dose is 20 mg of Compound 1 administered p.o. once daily.

* * * * *

UNITED STATES PATENT AND TRADEMARK OFFICE
CERTIFICATE OF CORRECTION

PATENT NO. : 8,785,484 B2  
APPLICATION NO. : 12/922777  
DATED : July 22, 2014  
INVENTOR(S) : Patrick Brossard et al.

Page 1 of 1

It is certified that error appears in the above-identified patent and that said Letters Patent is hereby corrected as shown below:

In the Claims

Claim 1, column 8, line 2, "during the an initial treatment phase Compound 1" should be changed to --during the initial treatment phase Compound 1--

Claim 5, column 10, second line, "according claim 1" should be changed to --according to claim 1--

Claim 6, column 10, second line, "according claim 3" should be changed to --according to claim 3--

Claim 7, column 10, second line, "according claim 1" should be changed to --according to claim 1--

Claim 8, column 10, second line, "according claim 3" should be changed to --according to claim 3--

Claim 9, column 10, second line, "according claim 5" should be changed to --according to claim 5--

Claim 10, column 10, second line, "according claim 6" should be changed to --according to claim 6--

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,785,484 B2                                   Page 1 of 1
APPLICATION NO.   : 12/922777
DATED             : July 22, 2014
INVENTOR(S)       : Patrick Brossard et al.

It is certified that error appears in the above-identified patent and that said Letters Patent is hereby corrected as shown below:

In the Claims

Claim 1, column 8, line 2, "during the an initial treatment phase Compound 1" should be changed to --during the initial treatment phase Compound 1--

Claim 5, column 8, line 23, "according claim 1" should be changed to --according to claim 1--

Claim 6, column 8, line 27, "according claim 3" should be changed to --according to claim 3--

Claim 7, column 8, line 31, "according claim 1" should be changed to --according to claim 1--

Claim 8, column 8, line 35, "according claim 3" should be changed to --according to claim 3--

Claim 9, column 8, line 39, "according claim 5" should be changed to --according to claim 5--

Claim 10, column 8, line 43, "according claim 6" should be changed to --according to claim 6--

This certificate supersedes the Certificate of Correction issued October 14, 2014.

Signed and Sealed this
Eleventh Day of November, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,785,484 B2 | Page 1 of 1 |
| APPLICATION NO. | : 12/922777 | |
| DATED | : July 22, 2014 | |
| INVENTOR(S) | : Brossard et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 457 days.

Signed and Sealed this
Eighth Day of September, 2015

Michelle K. Lee
*Director of the United States Patent and Trademark Office*